(12) United States Patent
Schoelling

(10) Patent No.: US 6,537,414 B1
(45) Date of Patent: Mar. 25, 2003

(54) SEALING ROLLER AND SEALING ROLLER ELEMENT PARTICULARLY FOR PRODUCING A TAMPON FOR FEMININE HYGIENE AND METHOD THEREFOR

(76) Inventor: Hans-Werner Schoelling, Dohlenweg 11, D58252 Ennepetal (DE)

( * ) Notice: Subject to any disclaimer, the term of this patent is extended or adjusted under 35 U.S.C. 154(b) by 0 days.

(21) Appl. No.: 09/606,958

(22) Filed: Jun. 29, 2000

Related U.S. Application Data

(60) Provisional application No. 60/141,688, filed on Jun. 30, 1999, and provisional application No. 60/141,690, filed on Jun. 30, 1999.

(51) Int. Cl.$^7$ ............................................. B32B 31/00
(52) U.S. Cl. ......................... 156/308.2; 156/308.4; 156/290; 156/324
(58) Field of Search .................... 156/290, 308.4, 156/308.2, 580, 324

(56) References Cited

U.S. PATENT DOCUMENTS

| | | | |
|---|---|---|---|
| 2,958,366 A | | 11/1960 | Conti |
| 3,015,996 A | * | 1/1962 | Ambler et al. |
| 3,153,607 A | * | 10/1964 | Ambler |
| 3,346,438 A | * | 10/1967 | Chavannes |
| 3,558,400 A | * | 1/1971 | Horvath et al. |
| 4,100,324 A | | 7/1978 | Anderson et al. |
| 4,436,576 A | * | 3/1984 | Seiden |
| 4,695,422 A | | 9/1987 | Curro et al. |
| 4,741,877 A | | 5/1988 | Mullane, Jr. |
| 4,816,100 A | | 3/1989 | Friese |
| 5,264,268 A | | 11/1993 | Luceri et al. |
| 5,403,300 A | | 4/1995 | Howarth |
| 5,567,376 A | | 10/1996 | Turi et al. |
| 5,634,914 A | * | 6/1997 | Wilkes et al. |

FOREIGN PATENT DOCUMENTS

| | | |
|---|---|---|
| DE | 1 560 128 | 2/1971 |
| EP | 0 295 957 | 12/1988 |
| EP | 0456281 A2 | 11/1991 |
| EP | 0738505 A1 | 10/1996 |
| EP | 0841156 A1 | 5/1998 |
| WO | WO 97/23185 | 7/1997 |
| WO | WO 98/20825 | 5/1998 |
| WO | WO 98/46182 | 10/1998 |
| WO | WO 99/00096 | 1/1999 |
| WO | WO 99/26769 | 6/1999 |
| WO | PCT/EP 00/06134 | 6/2000 |
| WO | PCT/EP 00/06135 | 6/2000 |

OTHER PUBLICATIONS

U.S. patent application Ser. No. 09/345,090 (PPC–691).
U.S. patent application Ser. No. 09/345,089 (PPC–713).
U.S. patent application Ser. No. 09/345,088 (PPC–708).
U.S. patent application Ser. No. 09/343,759 (PPC–668).
U.S. patent application Ser. No. 09/343,760 (J&J 1810).
U.S. patent application Ser. No. 60/141,688 (J&J 1819).
U.S. patent application Ser. No. 60/141,690 (J&J 1820).
U.S. patent application Ser. No. 09/606,559 (J&J 1924).
U.S. patent application Ser. No. 09/607,032 (J&J 1925).

* cited by examiner

*Primary Examiner*—Jeff H. Aftergut

(57) ABSTRACT

An apparatus for thermally bonding a cover material onto an absorbent, fibrous web has a substantially cylindrical, rotatable sealing roller and a rotatable anvil roller disposed adjacent the sealing roller to provide a nip therebetween. The cover material and fibrous web can be sealed and calendered in the nip of this apparatus. The sealing roller includes a sealing element and an ironing element, and both of these elements have thermally conductive material and a leading and a trailing end in the direction of rotation. The sealing roller has at least one pair of sealing and ironing elements positioned sequentially on the circumferential surface of the sealing roller in the direction of rotation. At least one end of the ironing element is thermally insulated from an adjacent end of an adjacent sealing element.

10 Claims, 2 Drawing Sheets

SEALING ROLLER AND SEALING ROLLER ELEMENT PARTICULARLY FOR PRODUCING A TAMPON FOR FEMININE HYGIENE AND METHOD THEREFOR

CROSS-REFERENCE TO RELATED APPLICATIONS

This application is related to the following applications: U.S. Ser. No. 09/343,759; U.S. Ser. No. 09/345,090; U.S. Ser. No. 09/345,089; U.S. Ser. No. 09/343,760; U.S. Ser. No. 09/345,088; U.S. Ser. No. 60/141,688; and U.S. Ser. No. 60/141,690; and claims benefit to these provisional applications; all filed on Jun. 30, 1999, and to and U.S. Ser. Nos. 09/607,032, and 09/606,559, filed on even date herewith, entitled "Tampon Having Apertured Film Cover Thermobonded to Fibrous Absorbent Structure" and "Tampon For Feminine Hygiene And Process And Apparatus For Its Production", respectively.

FIELD OF THE INVENTION

The invention relates to a sealing roller, particularly for a device for producing a tampon for feminine hygiene as well as a method for producing a tampon.

BACKGROUND OF THE INVENTION

Friese, U.S. Pat. No. 4,816,100 discloses a method and a device for producing a tampon for the feminine hygiene. The method includes sectioning a fluid permeable and at least partially thermoplastic material and heat sealing it onto an absorbent nonwoven fiber material or fleece web. Individual sections of the absorbent are severed from the fleece web supply and are wound onto themselves to form a tampon blank having a withdrawal cord. Thereby the fluid permeable cover material is positioned on the circumference of the tampon blank and surrounds it essentially completely. Finally, the tampon blank is pressed radially into the final shape of the tampon. Friese also employs a sealing roller to heat sealing the cover material onto the fleece web or the fleece web section. The sealing roller of Friese comprises heatable sealing elements that are spaced apart around the circumference of the sealing roller. Insulating means are arranged between these sealing elements. Thus, the sealing roller sealing elements and insulating elements alternate about the surface of the sealing roller in the direction of rotation.

Wilkes et al., U.S. Pat. No. 5,634,914, discloses multilimbed regenerated cellulose fibers which patentee claims provide high absorbency and a cotton-like handle. These tampons are described as having good stability and absorbency. Longitudinally-expanding tampons having these fibers are described as having less expansion than conventional longitudinally-expanding tampons.

Finally, Nguyen et al., WO97/23185 discloses tampons that can expand in the presence of high humidity after insertion into a user's body to prevent early bypass leakage from occurring. This tampon is a substantially cylindrical mass of compressed fibers enclosed within a fluid-permeable cover. The tampon has a stability of at least about 15 N, and is capable of radially expanding upon exposure to a humid environment. The radius increases by at least about 10% after 15 minutes to 90% relative humidity at 40° C. Particularly useful in this tampon are multilimbed fibes such as those in Wilkes et al. These fibers are relatively stiff to help the early expansion of the tampons.

Unfortunately processing these fibers causes difficulty, especially when a fibrous web having stiff fibers, such as the multilimbed fibers of Wilkes, are exposed to unexpected or undesired delays during manufacture. Such delays can allow previously calendered or compressed fibrous webs to bloom or expand, possibly due to humidity, as described in Nguyen et al. This expansion can cause jams or other undesirable process interruption.

Therefore, what is needed is a device and process to produce a high-quality tampon that secures a sufficient calendering of the fibrous fleece web for fibers that are otherwise hard to maintain in a compressed condition at a low cost.

SUMMARY OF THE INVENTION

An apparatus for thermally bonding a cover material onto an absorbent, fibrous web has a substantially cylindrical, rotatable sealing roller and a rotatable anvil roller disposed adjacent the sealing roller to provide a nip therebetween. The cover material and fibrous web can be sealed and calendered in the nip of this apparatus. The sealing roller includes a sealing element and an ironing element, and both of these elements have thermally conductive material and a leading and a trailing end in the direction of rotation. The sealing roller has at least one pair of sealing and ironing elements positioned sequentially on the circumferential surface of the sealing roller in the direction of rotation. At least one end of the ironing element is thermally insulated from an adjacent end of an adjacent sealing element.

The process for producing a tampon includes the following steps: a) applying a cover sheet to a fibrous web; b) passing the fibrous web and cover sheet combination through the nip of a sealing roller and an anvil roller; c) applying heat to a first portion of the combination at a first temperature range sufficient to bond the cover sheet to the absorbent web; and d) applying heat to a second portion of the combination at a second temperature range insufficient to bond the cover sheet to the absorbent web and sufficient to calender the fibrous web. The sealing roller provides heat at both the first and second temperature ranges to the cover sheet and fibrous web combination.

Again, it is an object of the invention to provide a device and a process to produce a high-quality tampon that secures a sufficient calendering of the fibrous fleece web for fibers that are otherwise hard to maintain in a compressed condition at a low cost device for producing a high-quality tampon which secures a sufficient calendering of the fleece web for fibers which are hard to calender at low cost. This object is solved by the apparatus including the sealing roller and the process of the present invention.

BRIEF DESCRIPTION OF THE INVENTION

DETAILED DESCRIPTION OF THE PREFERRED EMBODIMENT

Figure 1:
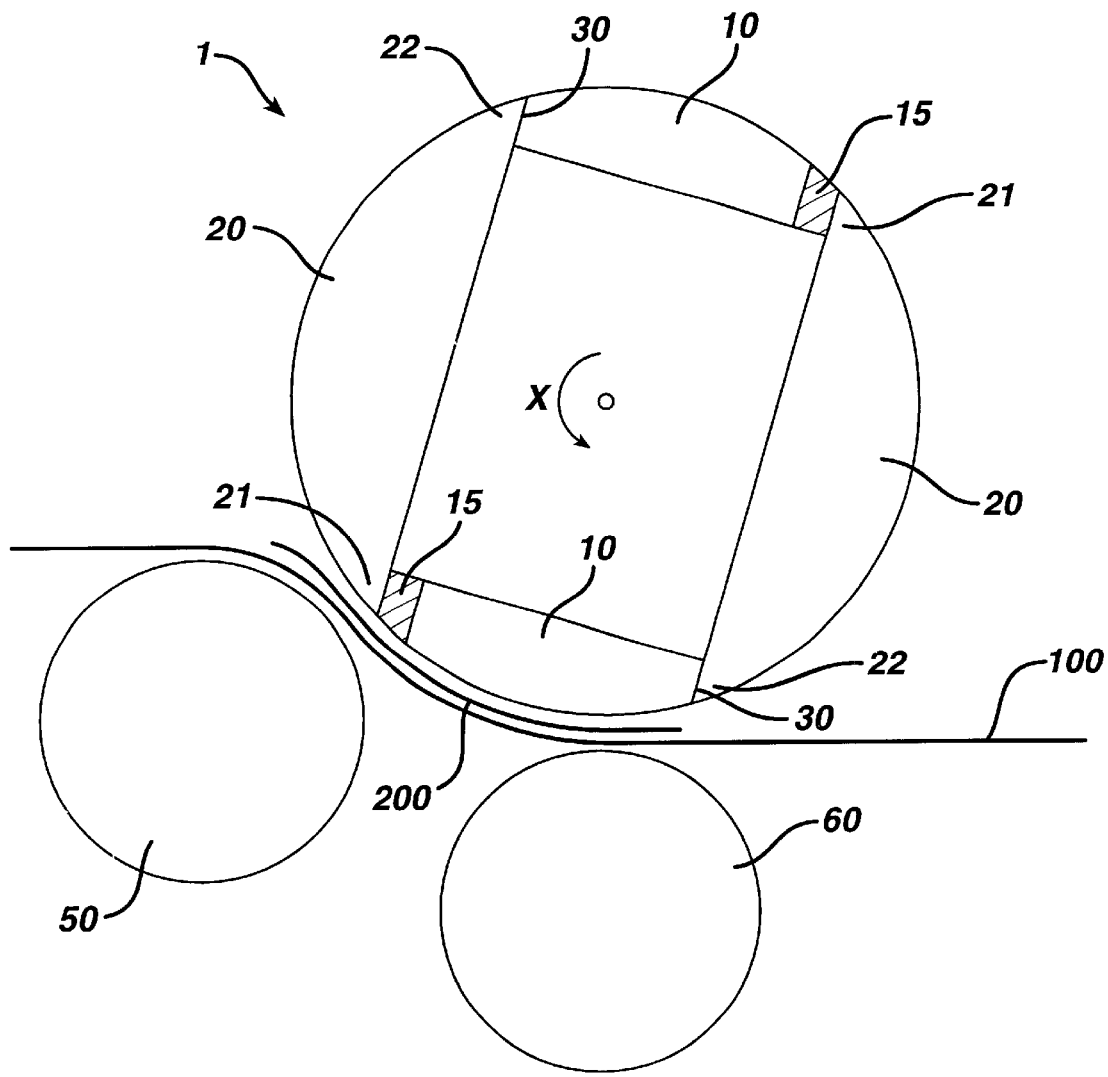
FIG. 1 shows diagrammatically in cross-section an embodiment of the inventive sealing roller.

In order to form the fleece web into the desired fleece thickness and fleece intensity, the fleece web usually is calendered, i.e., pressure and temperature are applied to it. Depending from the kind of fibers used for the fleece web, it turned out to be problematic that the fleece web is not sufficiently treated by standard calendering so that only a"subcalendering" takes place. In order to achieve the desired fleece thickness and intensity of the fleece web, some fibers, especially the fibers which are preferred because of their higher absorptive capacity, require several calendering steps which in the production process is complicated and, thus, expensive.

According to the invention, the sealing roller having at least one sealing element located at the circumference of the se ling roller comprises at least one heatable ironing element consisting of thermally conducting material that is thermally separated at at least one end from at least one adjacent sealing element. "Thermally separated" in this case means that there is essentially no, or in comparison with the relevant heating energies or energy differences, no considerable heat transport between the elements, so that the elements are at least largely insulated against each other.

Thus, it is achieved that pressure and temperature are applied to the fleece web at its entire length by the sealing roller. In addition to the original object of the sealing roller, namely the sealing of cover material onto the fleece web, the fleece web is ironed and calendered without requiring a further process step or an additional device for the already complex and expensive processes or process machines, respectively. Even hard to calender fibers are reliably and durably formed into the desired shape by the repeated ironing or calendering respectively.

The fleece web may include any absorbent materials that are capable of absorbing and/or retaining liquids (e.g., menses). The absorbent structure can be manufactured in a wide variety of sizes and shapes and from a wide variety of liquid-absorbing materials. A representative, non-limiting list of useful materials includes cellulosic materials, such as rayon, cotton, wood pulp, creped cellulose wadding, tissue wraps and laminates, peat moss, and chemically stiffened, modified, or cross-linked cellulosic fibers; polymeric materials, such as polyester fibers, polyolefin fibers, absorbent foams, absorbent sponges, superabsorbent polymers, absorbent gelling materials; formed fibers, such as capillary channel fibers and multilimbed fibers; combinations of materials, such as synthetic fibers and wood pulp including coformed fibrous structures (e.g., those materials described in Anderson et al., U.S. Pat. No. 4,100,324); or any equivalent material or combinations of materials, or mixtures of these. However, the present invention is particularly useful for processing fleece webs containing multilimbed fibers, such as those disclosed in Wilkes, U.S. Pat. No. 5,634,914, the disclosure of which is herein incorporated by reference.

Useful cover materials used in conjunction with the present invention will be recognized by the ordinarily skilled practitioner. Known cover materials include woven, knit, and nonwoven fabrics; two-dimensional and three-dimensional apertured films; polymeric nets; and the like. Preferably, the cover material is a nonwoven fabric or a three-dimensional apertured film. Such nonwoven materials are disclosed in Friese, U.S. Pat. No. 4,816,100, the disclosure of which is herein incorporated by reference. In addition, the apertured film cover of the present invention can be manufactured by standard processes known to those of ordinary skill in the art. For example, the base film that is to be apertured can be extruded, cast, or blown to form the film. The base film can be a single formulated polymeric material or blend, or it can be a laminated or multi-layered material such as described in commonly assigned, co-pending applications to Johnson et al., U.S. Ser. No., 09/345,090, and Gell et al., U.S. Ser. No., 09/345,089, the disclosures of which are herein incorporated by reference. Useful technology to form these films will be easily recognized by those of ordinary skill in the art. The base film can then be apertured by any useful process. Several examples include hot air aperturing, and water jet aperturing. Examples of these processes are disclosed in Curro, U.S. Pat. No. 4,695,422; Turi, U.S. Pat. No. 5,567,376; and Mullane, U.S. Pat. No. 4,741,877; the disclosures of each of these patents are hereby incorporated by reference. The resulting apertured film can be coated, for example as described in commonly assigned, co-pending application U.S. Ser. No., 09/345,088, filed Jun. 30, 1999, entitled"Tampon with Cover and Nonionic Surfactant", and/or slit to a desired width for use in manufacturing a tampon.

In a preferred embodiment, the rear end of the at least one ironing element, as seen from the rotating direction of the sealing roller, is in thermal contact with the sealing element positioned behind the ironing element in the rotating direction and the front end in the rotating direction of the at least one ironing element is separated from the heatable sealing element which is located in front of the ironing element when seen from the direction of rotation. Thus, the ironing element is heated indirectly via the thermal contact of the sealing element. An additional heating device for the ironing element is not required. Moreover, the temperature of the ironing element is automatically adapted to the desired temperature predetermined or required for the heat sealing. The temperature applied to the fleece web slowly decreases from the highest temperature at the sealing element adjacent an insulating element or space to the front end of the ironing element and finally to the rear end of the ironing element to constantly calender the fleece web.

It is additionally guaranteed that a maximum temperature of the ironing element is not exceeded in the area in which a heat sealing of the cover material is to be prevented. An undesirable heat sealing of the cover material onto the fleece web is prevented and at the same time the fleece web material is ironed and calendered whereby a remarkably improved fiber structure of the fleece web is achieved.

The material of the ironing element may be chosen from numerous thermally conducting materials. In general, metals, in particular aluminum, are the preferred materials. Depending on the choice of material and the corresponding heat conductivity, the course of temperature or the temperature gradient respectively may be determined in case of an above-mentioned partial thermal contact and optimally adapted to the material in use of either the fleece web and the cover material.

The thermally separated ends of the ironing element and the sealing element are preferably spaced apart in a predetermined distance so that an insulating air aperture is formed. it is also possible to place an insulating element between the thermally separated elements. Preferably, the sealing element and the ironing element are not completely thermally separated. However, the desired level of insulation may be determined in relation to the chosen spaces between the elements or the applied insulating elements. The heat conductivity or the heat contact respectively of the ends of the ironing element and the sealing element being in thermal contact may considerably be improved if the ironing element and the sealing element at least partially overlap and/or are at least partially interlocked. The overlapping may be realized wherein the end portion of the sealing element is graded or inclined and is located below or above a correspondingly formed end portion of the ironing element and is engaged with it. This overlapping may also be regarded and designated as a"radial interlocking". A second possibility is an at least partial interlocking of both elements at the outer surface, in general in a coaxial rotating direction of the sealing roller.

In a preferred embodiment, the sealing roller comprises two diametrically opposed sealing elements and two diametrically opposed ironing elements. This results for usual lengths of the cover material, which is applied in the form of strips of the fleece web section, respectively, in a simple and easy-to-realize geometry and dimension of the sealing roller. Thus, the desired geometrical arrangement of the ironing elements and the sealing elements is secured without requiring a great curvature of the surfaces of the elements resulting from a sealing roller having a small diameter. Naturally, it is possible to arrange only one sealing element and one ironing element or more than two sealing elements and two ironing elements alternately. The dimension of the sealing roller increases with the number of sealing and ironing elements provided for, since the circumferential length of the single elements depend from the geometry of the materials to be treated, the cover material and the fleece web section, as explained above.

Preferably, the temperature of the sealing elements is adjustable by a control to allow adjustment of the sealing element temperature to maintain it at a desired target temperature. Appropriate thermal sensors may be used to monitor the temperature. The adjustable temperature control allows the device to be adapted to the materials to be processed, so that a variety of fibers and cover materials such as those materials described above may be processed in a high quality manner.

In another embodiment, in addition to the sealing elements, the ironing elements are directly heatable. Thus, further possibilities for the temperature control of the ironing elements exist, the ironing elements especially have a constant temperature without any temperature gradient along their entire area in care this is desired for the final product to be processed. In such an embodiment, it is likely that both ends of each ironing element are thermally separated from adjacent sealing elements.

The invention further relates to a method for producing a tampon for feminine hygiene. In particular, it relates to a method involving thermally sealing an at least partially thermoplastic cover material to a fleece web at a desired sealing temperature. The method according to the invention also provides for ironing the fleece web at an ironing temperature at a location between the areas of the cover material that are sealed whereby the maximum ironing temperature does not exceed the sealing temperature. In the areas in which the ironing element works on the cover material, the ironing temperature should not be high enough to cause unintentional sealing or damage to the cover material. As described above in connection with the device according to the invention, by such method, the fleece web is at the same time calendered over its surface by the required sealing process, i.e., pressure and temperature are applied. The desired fleece web structure and fleece web thickness is secured without the requirement of a new process station and additional devices.

The preferred sealing temperature is 140° C. for the preferred fleece web containing cotton and rayon or rayon blends and a cover material containing polyethylene. This provides a reliable heat sealing of the materials in use. The cover material is reliably bonded with the fleece web section in the desired bond region while the rest of the cover material attains a temperature that does not cause it to bond or otherwise be damaged.

In another embodiment of the method according to the invention, the ironing temperature is essentially constant which is preferably realized by a separate heating of the ironing element. With this method, one end of the ironing element may be in thermal contact with the sealing element leading at least in a partial area of the ironing element to a temperature gradient or the sealing element may be thermally completely separated, the latter being the preferred variation.

FIG. 1 shows an embodiment of an inventive sealing roller 1 having two sealing elements 10 arranged diametrically facing each other and two ironing elements 20 arranged between the sealing elements 10, said ironing elements 20 diametrically facing each other. The circumferential length of the sealing elements 10 corresponds exactly to the length of a range of a fleece web 100 to be sealed onto the cover material 200.

The sealing elements 10 as well as the ironing elements 20 are made of a thermally conductive material. A representative, non-limiting list of materials includes metals such as steel, including stainless steel, mild steel, tool steel, and the like; and aluminum. Useful stainless steels include the 300 series including 303, 304, and 316; the 400 series, and the 800 series. Useful mild steels include 1018 and 1020. Useful aluminum alloys include the 2000 series including 2024; the 3000 series including 3003; the 5000 series including 5052 and 5080; the 6000 series including 6061, 6063, and 6082; and the 7000 series including 7075. These materials can be coated with appropriate coatings to protect the sealing element from corrosion and wear and to reduce the likelihood of the sealed material from adhering to the tooling surfaces. Such materials will be recognized by those of ordinary skill in the art.

Heating elements are associated with the sealing elements 10 in a manner to provide well-controlled heat to the sealing bars 16. Preferably, the heating elements controllable to provide a heat accuracy of +/– 5° C., more preferably, about +/– 2° C. This can be achieved by placing, e.g., two heating elements symmetric to a middle plane of the sealing element 10, or three or more elements in appropriate locations on the sealing element. Alternatively, it is possible to employ a single plate heating element or to incorporate conduits within the sealing element 10 to accommodate a circulated heating fluid. In addition, a temperature control element, such as a thermocouple, can be provided close to the sealing surfaces, e.g., at the middle plane of the sealing element 10.

The ends 22 of the ironing elements 20 which, in the direction of rotation of sealing roller 1, marked by arrow x, are positioned at the rear end, are in thermal contact with each sealing element 10 positioned back of it. The ends of the ironing elements 20 being the front ends 21 in the direction of rotation are thermally separated from each sealing element 10 positioned in front of it. The thermal separation can be simply realized by an air gap. In the current embodiment, however, the use of a high heat insulating plastic element 15 is intended.

In operation the sealing elements 10 are heated up to a temperature of 140° C. Via a thermal contact 30 heat energy is transferred from the sealing element 10 to the ironing element 20 so that each ironing element 20 has also a temperature of 140° C. at its rear end in close proximity to the thermal contact 30. The ironing elements 20 show a temperature gradient because of the existing cooling so that in the current embodiment there is a temperature of about 80° C. at a front end 21 of each of the ironing elements 20 being separated from the sealing element 10 next to it by the insulating elements 15.

A pressure roller 50 presses the fleece web 100 against the sealing roller so that the cover material 200 is securely sealed onto the fleece web by sealing elements 10. Furthermore, it is provided for another transport and/or driving roller 60 that drives the fleece web 100 and/or holds it in the desired position.

Figure 2:
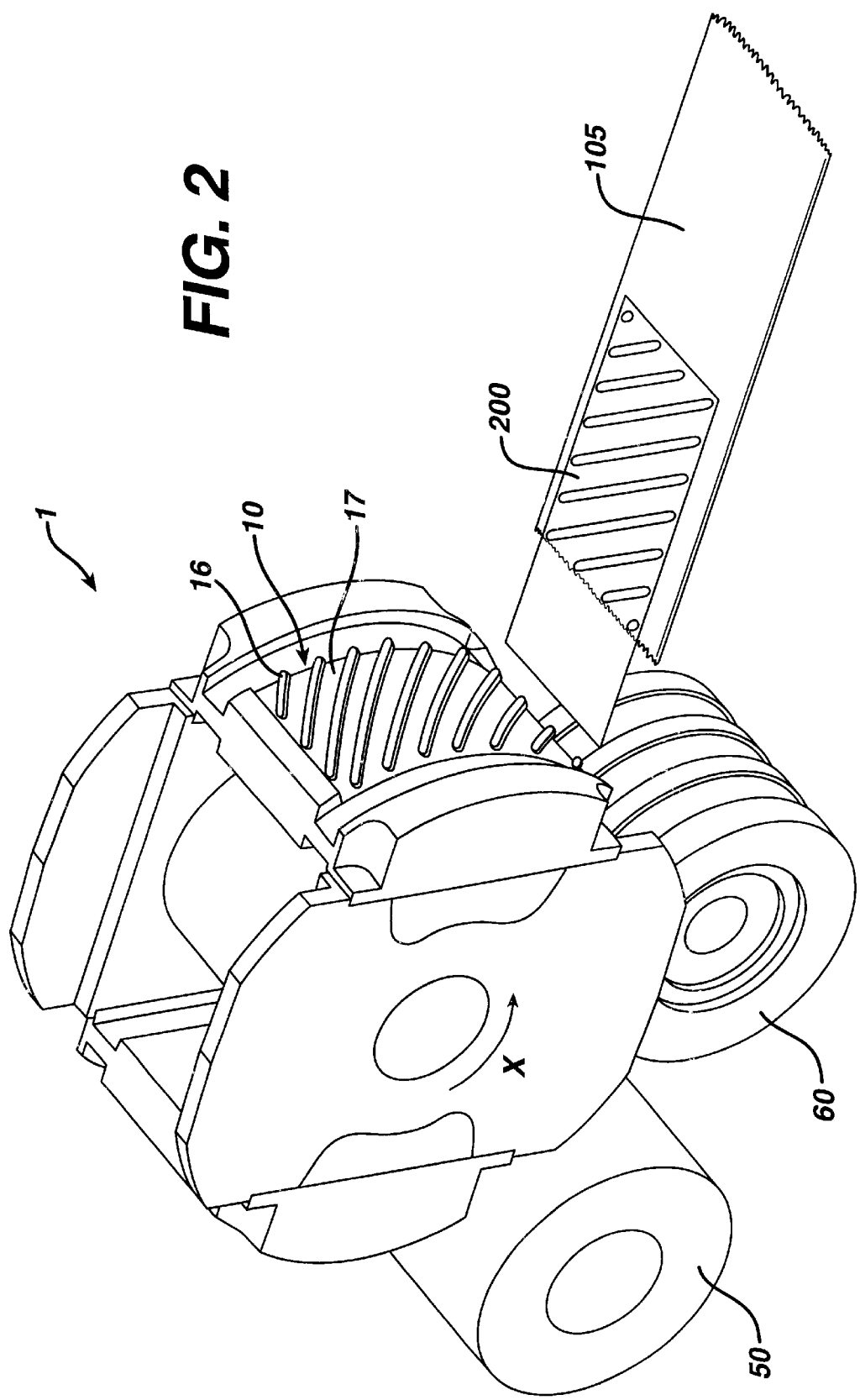
FIG. 2 shows in an perspective view another embodiment of an inventive sealing roller and a fleece web section with cover material sealed onto it.

FIG. 2 shows a perspective view of a further embodiment of an inventive sealing roller as well as a fleece web auction 105 with a strip of cover material 200 sealed onto it. The sealing elements 10 comprise sealing bars 16 arranged in transverse rows and at distances from one another with said sealing bars projecting about 0.3 cm from a base 17 of the sealing elements 10.

The ironing elements 20 are not shown in FIG. 2, they merely consist of circle segments with a substantially smooth but curved surface which can be inserted into the sealing roller 1. By a possible exchange of the ironing elements 20 the temperature and especially the temperature gradient of the ironing elements can be adapted to the desired object and the used materials, respectively in dependence on the material and its thermal conductivity. As shown in the embodiment of FIG. 1, the thermal contact is provided for between the ends being the rear ends of the ironing elements 20 in the direction of rotation x and the respective sealing elements 10 positioned back of it whereas the ends being the front ends 21 of the ironing elements 20 in the direction of rotation x are separated from the respective sealing elements 10 positioned in front of it after the ironing elements having boon inserted into the sealing roller 1.

It is again to be stated that in the scope of the invention further variations of the sealing bars are possible and applicable. In addition to sealing the cover to the fleece web, the sealing bars 16 of the sealing element 10 can extend beyond the cover material to additional compress or calender the fleece web. This provides further beneficial calendering to stiff fibers that may be included in the fleece web.

The drawings are merely diagrammatical and not in the real ratio of dimensions so that no limitations can be deducted from the concrete dimensions.

The features disclosed in claims, specification and drawings can be substantial for the invention, either solely or in any possible combination.

What is claimed is:

1. A process for producing a tampon comprising the steps of:
   a) applying a cover sheet comprising thermoplastic material to a fibrous web comprising stiff fibers;
   b) passing the fibrous web and cover sheet through the nip of a sealing roller and an anvil roller;
   c) applying heat to a first portion of the cover sheet and fibrous web combination at a first temperature range sufficient to bond the cover sheet to the absorbent web;
   d) applying heat to a second portion of the cover sheet and fibrous web combination at a second temperature range insufficient to bond the cover sheet to the absorbent web and sufficient to calender the fibrous web
   wherein the sealing roller provides heat at both the first and second temperature ranges to the cover sheet and fibrous web combination.

2. The process of claim 1 wherein the first temperature range is greater than the softening point of the thermoplastic material in the cover sheet.

3. The process of claim 2 wherein the first temperature range is greater than the melting point of the thermoplastic material in the cover sheet.

4. The process of claim 1 wherein the second temperature range is less than the softening point of the thermoplastic material in the cover sheet.

5. The process of claim 1 wherein the second temperature range is substantially constant.

6. The process of claim 1 wherein the second temperature range increases during passage of the cover sheet and fibrous web combination through the nip.

7. The process of claim 6 wherein the second temperature range is from about 80° C. to about 140° C.

8. The process of claim 1 wherein the fibrous web comprises multilimbed fibers.

9. The process of claim 1 wherein the fibrous web comprises multilimbed rayon fibers.

10. The process of claim 8 wherein the fibrous web comprises multilimbed polyester fibers.

* * * * *